(12) United States Patent
Traylor, III

(10) Patent No.: US 6,596,153 B1
(45) Date of Patent: Jul. 22, 2003

(54) METHOD FOR ANALYZING A GAS SAMPLE

(75) Inventor: Frank A. Traylor, III, Littleton, CO (US)

(73) Assignee: Lifeloc Technologies, Inc., Wheat Ridge, CO (US)

( * ) Notice: Subject to any disclaimer, the term of this patent is extended or adjusted under 35 U.S.C. 154(b) by 105 days.

(21) Appl. No.: 09/615,004

(22) Filed: Jul. 11, 2000

(51) Int. Cl.[7] .............. G01N 27/16; G01N 1/22
(52) U.S. Cl. ............ 205/775; 205/787; 422/84; 73/23.3
(58) Field of Search ............. 422/83, 84; 73/23.21, 73/23.3; 205/775, 787; 204/400, 406, 407

(56) References Cited

U.S. PATENT DOCUMENTS

| 4,770,026 A | 9/1988 | Wolf | 422/84 |
| 5,393,495 A | 2/1995 | Forrester | 422/83 |
| 5,458,853 A | 10/1995 | Porter et al. | 422/84 |
| 5,612,896 A | 3/1997 | Stock | 205/775 |

OTHER PUBLICATIONS

Huck, Electroanalytical Chemistry and Interfacial Electrochemistry, 53, pp. 121–132, 1974.*
Certified translation of Huck, Electroanalytical Chemistry and Interfacial Electrochemistry, 53, pp. 121–132, 1974.*
CAPLUS abstract for Huck, J. Electroanal. Chem. Interfacial Electrochem. (1974), 53(1), pp. 121–132.*

* cited by examiner

Primary Examiner—Nam Nguyen
Assistant Examiner—Kaj K. Olsen
(74) Attorney, Agent, or Firm—Merchant & Gould P.C.

(57) ABSTRACT

A method for determining the quantity and identity of an electrochemically convertible substance in a gas sample. The substance is converted in an electrochemical sensor producing an electrical output. The characteristic parameters of a curve-defining equation $y(t)=k \times (e^{-axt}-e^{-bxt})$ are calculated based on three measurements of output at times t, 2t, and 4t. The integral under all or part of the curve is calculated to determine the quantity of the substance. The equation parameters are compared with standard values to determine the identity of the substance.

14 Claims, 1 Drawing Sheet

METHOD FOR ANALYZING A GAS SAMPLE

BACKGROUND OF THE INVENTION

1. Field of the Invention

This invention relates to a method for quantifying and identifying an electrochemically convertible substance in a gas sample. More specifically, the invention relates to a method for determining breath alcohol content quantitatively and for distinguishing and identifying other electrochemically convertible substances.

2. Description of the Prior Art

Handheld breath alcohol testing devices have proved useful in roadside estimation of blood alcohol level of drivers. Electrochemical sensors are commonly used in these devices. In the typical arrangement, a sample of gas is introduced into the electrochemical sensor and a current is generated by the oxidation of the alcohol. The electrical output from the sensor increases from an initial value to a peak and then decreases back to at or near the initial value. These output amplitude measurements, plotted over time, form a curve hereafter referred to as the output curve. Electrochemical sensors exhibit some problems.

The first problem arises because errors in the measurement in breath alcohol content are introduced because the shape of the output curve is affected by variations in temperature, repeated use of the sensor, and aging of the sensor. In prior methods, the imprecision occurring due to the aforementioned variables, will alter the peak of the curve and, in turn, the measurement result.

A method disclosed in U.S. Pat. No. 4,770,026 attempts to overcome the dependencies of the output curve on these variables. In the known arrangement, the output measurements are summed to provide the integral of the entire output curve. This integral is the total area under the output curve and therefore represents the total current derived from the oxidation of the alcohol and therefore is proportional to the alcohol concentration in the sample. This method, however, requires the summation of the entire output curve without determining any curve fit function, making the measurement time prohibitively long.

A method of reducing this measurement time is disclosed in U.S. Pat. No. 5,393,495. This patent acknowledges the discovery that the amount of the reactant is proportional to the integral of the electrochemical sensor output curve. This method, however, finds the integral of a lognormal curve fit equation that approximates the sensor output curve. This method has the advantage that the integral for the lognormal curve can be calculated as soon as its equation is derived. This allows a shorter measurement time. The lognormal equation, being only a rough approximation of the output curve, yields the most accurate results only when it is based on a long measurement time and is less accurate when derived after a short time. The known method, therefore, still requires a long measurement time to achieve the highest accuracy.

Another problem with measuring alcohol in the breath is presented by the possibility of contaminants. While ethanol can be oxidized by the electrochemical sensor and produce an electrical output, so can other volatile substances such as methanol and isopropanol. The presence and oxidation of these contaminants changes the output curve and in turn the estimate of ethanol in the breath. A method is disclosed in U.S. Pat. No. 5,612,896 in which the areas under specific sections of the output curve are calculated and compared. The relationship of these areas gives an indication of the substances being reacted. This method requires that the output curve decline to at least 6% of its maximum value, thus requiring an extended measurement time, especially at low temperatures.

Porter, U.S. Pat. No. 5,458,853 is merely a two stage breathalyzer to save the cost of using a mouth piece for each test when it may not be necessary. Porter does disclose an exponential equation for a fuel cell's function similar to one disclosed, used and claimed herein. Porter's use of the equation is limited to transformation manipulation to isolate the reaction constant of the fuel cell and thus enable the preliminary test to detect the presence of alcohol.

The Porter apparatus and disclosure makes use of prior art methods of calculation and determination of breath analysis. Porter views the exponential equation as lacking stability and precision for calculation of alcohol.

OBJECTS OF THE INVENTION

It is the principal object of the present invention to provide an improved method of gas analysis which reduces the amount of time required for a measurement and improves the accuracy of measurement.

Another object of the invention is to provide a method of the foregoing character which facilitates identification of the reactants and reduces measurement errors.

Further objects and advantages of the invention will become apparent from a consideration of the drawings and ensuing description.

SUMMARY OF INVENTION

The method according to the invention includes the steps of: measuring the electrical output of an electrochemical sensor on a periodic basis, using these measurements to calculate an exponential fit equation that approximates the sensor output, integrating the equation to approximate the area under the output curve, and using the parameters of the equation to determine the type of substance being reacted.

The improvement of this method is based on the discovery of an equation that precisely matches the electrochemical sensor output curve and the characteristics of the reaction itself. The reaction and the discharge in the electrochemical sensor are exponential decay functions. The discovered exponential fit equation consists of multiple exponential parameters and a magnitude parameter. One of the exponential parameters in the equation represents the reaction. Another exponential parameter represents the discharge of the sensor. The exponential fit curve parameters are determined after a short amount of time and thus provide a fast and accurate quantification of reactant, independent of temperature, repeated testing, and sensor age. The curve parameters additionally allow identification of the reactant. As contemplated the curve fitting is based on a selected electrochemically reactive compound. The equation constants for that reactant are known and used as a standard against which the actual sample is compared. If there are contaminates or if the tested reactant differs from the target reactant, the equation fitting the actual results will differ from the standard equation, this may be by superposition of multiple curves due to a contaminate adding its curve fitting equation to the standard or targeted curve fitting equation. Thus in a particular sample, the curve fitting equation may not match the targeted reactant but may match other known reactants. Alternatively, the tested sample may have two or more exponential components with different constants representing the contribution of the two or more different reactants present in the sample and their different reaction constants and concurrently the two or more different constants for the discharge constants would be present as there would be concurrent multiple exponential components for the discharge component of the actual sample curve. A further advantage of this method is to test if the sample is contaminated by other types of reactants, and if not, then determine the total of the reactant and thus the quantity of the targeted reactant, i.e. ethanol or other desired products.

The early determination of the exponential fit curve provides a quantification of the reacting substance before the entire output curve has been measured. The accuracy of the present invention is not compromised by an early measurement time because the present invention discloses an equation that very precisely matches the sensor output curve.

The present invention provides a precise calculation of the true reaction parameters at an early time in the reaction cycle yielding a faster and more accurate determination.

The equation disclosed is of the general form $y(t) = k \times (e^{-axt} - e^{-bxt})$ where $y(t)$ is the amplitude of the output curve at time t, k is the amplitude factor, b is the reaction factor, and a is the discharge factor. Three measurements are needed to solve for the three parameters; the first measurement is at any time (t) from the start of the curve, the second measurement at twice this time (2t) from the start of the curve, and the third measurement four times this time (4t) from the start of the curve. Solving the equation using these measurements yields the three factors; k, a, and b, and therefore, the characterization of the entire electrochemical sensor output curve.

Other useful results can be derived once the exponential fit curve equation has been determined:

(1) The total area under the exponential fit curve, and therefore the quantity of reactant, can be determined by integrating the exponential fit curve from zero to infinity.

(2) The area under any curve segment can be found by integrating the exponential fit equation between the time at the start of the segment and the time at the end of the segment.

(3) The area under any curve segments between given sensor output amplitudes can be found by using the using the exponential fit equation to solve for the times corresponding to the magnitudes and then integrating between these times.

(4) The time of the peak of the exponential fit curve can be determined by solving the first derivative of the exponential fit equation for zero.

(5) The peak measurement can be found by solving the exponential fit equation for the peak time.

(6) The inflection point of the exponential fit tail can be determined by solving the second derivative of the exponential fit equation for zero.

(7) The "b" factor is equivalent to the rate of reaction in the electrochemical sensor, and the "a" factor is equivalent to the rate of discharge. Different substances react at different rates and thus yield different "a" and "b" factors. Once these factors are determined they can be compared to characteristics of known reacting substances to determine the reactant type.

DESCRIPTION OF THE PREFERRED EMBODIMENT

Figure 1:
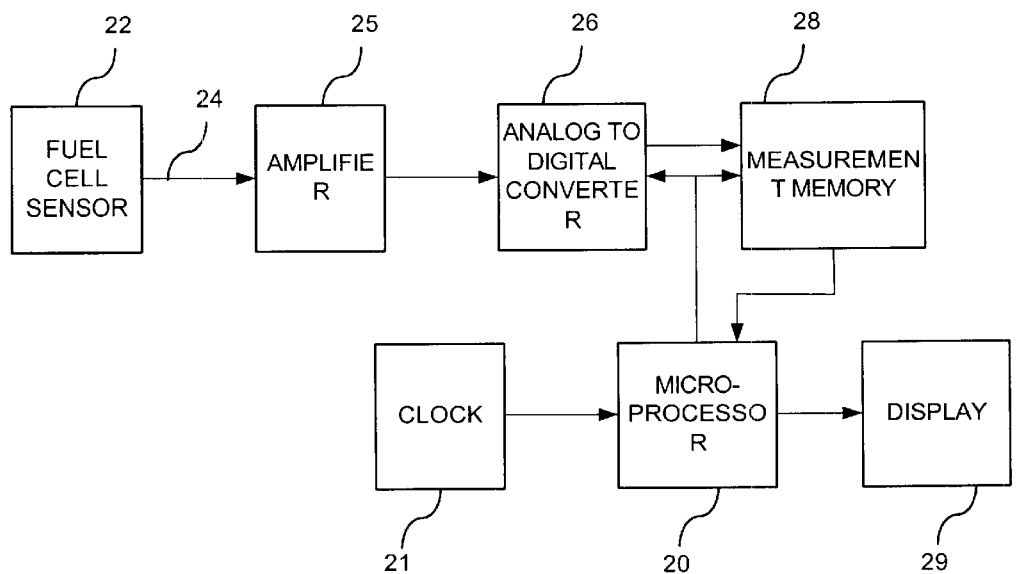
FIG. 1 is a block diagram showing the electronic circuit of a gas analysis apparatus embodying the present invention.

Referring now to FIG. 1 showing apparatus incorporating an electronic circuit utilizing the method of the present invention, the microprocessor 20 reads the clock 21 and records the start time upon introduction of a gas sample into the electrochemical fuel cell sensor 22. The output 24 of the sensor 22 is amplified by an amplifier 25 and input to an analog to digital converter 26. At predefined periodic intervals after the start time the microprocessor 20 signals the analog to digital converter 26 and a measurement memory 28 to record a measurement. This signal causes the analog to digital converter 26 to latch the analog sensor output amplitude and causes the measurement memory 28 to read the digital representation of this amplitude, which may be a current or voltage value. The microprocessor reads measurements from the measurement memory 28, calculates the equation or curve parameters, calculates the quantity of reactant, and displays the result on the display 29. To this end, the microprocessor is programmed to solve the following equations according to the measurements.

I have discovered that the basic or principal equation utilizable by the microprocessor 20 to produce the desired analytical results is $y(t) = k \times (e^{-axt} - e^{-bxt})$, in which "b" represents the fuel cell reaction rate, "a" represents the fuel cell discharge rate, and "k" is the amplitude factor. This equation defines a curve that, starting at zero output and time, rapidly reaches a peak output and then slowly declines over time toward a zero output at infinite time.

The equation factors or parameters k, a, and b, are calculated in the microprocessor by retrieving three sensor output measurements, one at time t; another at twice that time, 2t; and a third at four times that time, 4t. The following equations, derived from the basic equation, are used by the microprocessor to determine the parameters a, b, and k:

$$a = -\frac{\ln\left[\left(\frac{y_{2t}}{y_t} + \sqrt{\left|2 * \frac{y_{4t}}{y_{2t}} - \left(\frac{y_{2t}}{y_t}\right)^2\right|}\right)/2\right]}{t}$$

$$b = -\frac{\ln\left[\left(\frac{y_{2t}}{y_t} - \sqrt{\left|2 * \frac{y_{4t}}{y_{2t}} - \left(\frac{y_{2t}}{y_t}\right)^2\right|}\right)/2\right]}{t}$$

$$k = \frac{y_t}{\sqrt{\left|2 * \frac{y_{4t}}{y_{2t}} - \left(\frac{y_{2t}}{y_t}\right)^2\right|}}$$

The area under exponential curve defined by the curve equation between any two times (t start and t stop) can be found by integrating the exponential equation between these times as limits. This integral is given by the equation:

$$Area = k \times \left(\frac{e^{-axt_{start}}}{a} - \frac{e^{-bxt_{start}}}{b} - \frac{e^{-axt_{stop}}}{a} + \frac{e^{-bxt_{stop}}}{b}\right)$$

For the integration under the entire output curve of the equation(t start=0 and t stop= ) the equation simplifies to:

$$Area = k \times \left(\frac{1}{a} - \frac{1}{b}\right)$$

Other important information can be derived from these factors or rate and magnitude parameters. The peak time (t peak) can be found by solving the first derivative of the exponential fit equation for zero. This results in the following solution for the peak time:

$$t_{peak} = \frac{\ln(a/b)}{a-b}$$

The magnitude of the peak of the curve can be found by solving the exponential fit equation for t peak resulting in the following solution:

$$y_{peak}(t) = k \times (e^{-axt_{peak}} - e^{bxt_{peak}})$$

The a factor indicates the rate of discharge in the electrochemical sensor and the b factor indicates the rate of reaction. Because different substances will react and discharge at different rates the a and b factors can be used to identify the reactant. The following table shows the relationship of a, b, and t peak for isopropanol and methanol related to the values for ethanol:

|  | a | b | t peak |
|---|---|---|---|
| Ethanol | 1.00 | 1.00 | 1.00 |
| Isopropanol | 0.95 | 1.35 | 0.83 |
| Methanol | 0.49 | 0.44 | 2.20 |

In the preferred embodiment, ethanol reference values for a, b, and t peak are stored during a calibration procedure. After each test, a, b, and t peak are compared to the reference values. As shown in the table, isopropanol will produce a value for b that is 1.35 times the ethanol reference value and a t peak of 0.83 times the ethanol reference value. Methanol provides values for both a and b that are less than half the reference values and a t peak that is 2.2 times the reference value. Such a comparison to the ethanol reference allows an identification of the reactant.

Because the exponential parameter equations use sets of measurements at time t, 2t, and 4t, new parameters for the equation can be produced after every fourth measurement. The sequence of results can be averaged to provide the most precise results.

The area under the curve defined by the equation is directly proportional to the alcohol content of the gas sample. This area is determined by integrating the equation, and applying a proportion factor to express the alcohol or other measured gas content of the gas sample.

Figure 2:
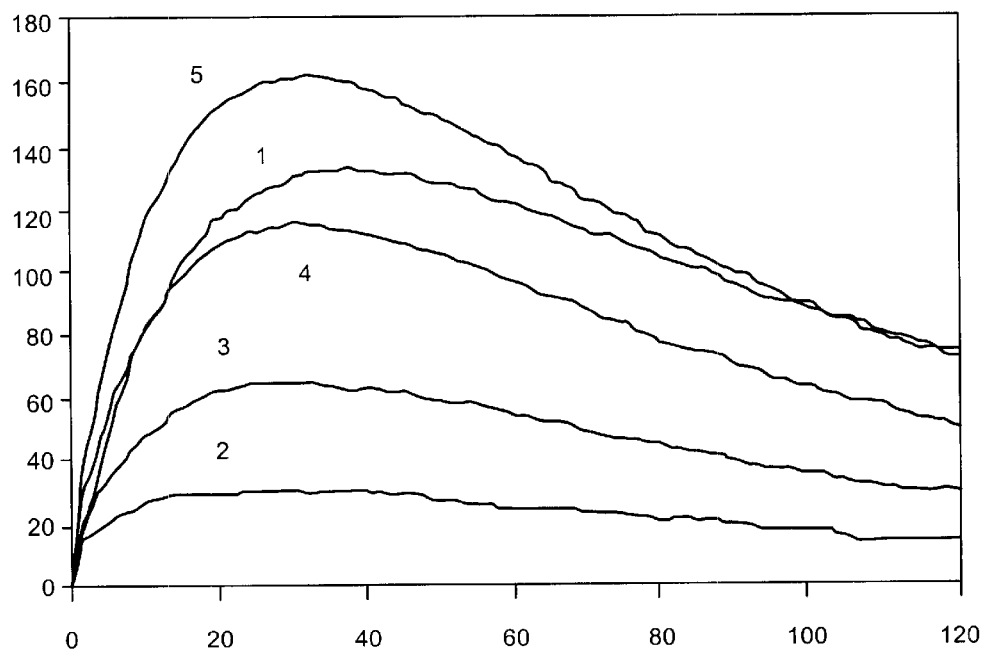
FIG. 2 is a chart showing output curves for trials described herein.

Measurements of gas samples with known concentrations of ethanol corresponding to blood alcohol content (BAC) were made on the apparatus embodying the method of the present invention. For each such gas sample, the method produced the results shown in Table I. In this table, the first column (Gas Sample 1) is a calibration. These results are plotted as curves 1, 2, 3, 4, and 5 in the chart shown in FIG. 2. The results demonstrate the utility of the method embodying the present invention in accurately analyzing alcohol containing gas samples.

TABLE I

| | GAS SAMPLE | | | | |
|---|---|---|---|---|---|
| | 1 | 2 | 3 | 4 | 5 |
| | Known Alcohol Concentration in Gas Sample (BAC) | | | | |
| | 0.100 | 0.020 | 0.040 | 0.07 | 0.100 |
| t | 30 | 30 | 30 | 30 | 30 |
| vt | 131 | 31 | 65 | 116 | 162 |
| v2t | 121 | 25 | 54 | 96 | 136 |
| v4t | 73 | 13 | 28 | 49 | 71 |
| a | 0.0092 | 0.0112 | 0.0114 | 0.0117 | 0.0114 |
| b | 0.0601 | 0.0799 | 0.0704 | 0.0696 | 0.0684 |
| k | 220.3 | 49.7 | 110.4 | 200.1 | 278.1 |
| alcohol | 20319.2 | 3825 | 8095 | 14203 | 20396 |
| Calibrate | 203192 | 203192 | 203192 | 203192 | 203192 |
| Factor Result | 0.100 | 0.019 | 0.040 | 0.070 | 0.100 |
| tpk | 36.9 | 28.6 | 30.8 | 30.8 | 31.5 |
| ypeak | 131 | 31 | 65 | 116 | 162 |

The method disclosed with further known calculations by the microprocessor can be used to compare and determine the tested sample's reactant identification. The comparison of the tested sample's exponential fit equation constants with stored values of fit equation constants of different reactants can be done and the output will identify the reactant tested.

As an additional embodiment, the microprocessor may be programmed by common methods to determine if the tested reactant's curve is a superposition of two or more reactants curves. If so, further tests can be done to determine the ethanol alcohol content in the subject. Also, the microprocessor can calculate and compare the tested sample's curve and its deviation from the target reactant or reactants' curves. If it meets a predetermined level of what deviation is acceptable, then the microprocessor finishes the desired calculations and determines the values desired.

What is claimed is:

1. A method of determining a quantity of an electrochemically convertible substance in a gas sample, the method comprising:

introducing the gas sample into an electrochemical sensor wherein at least a portion of the gas sample is electrochemically converted to produce an electrical output;

measuring the electrical output of the electrochemical sensor at three or more time intervals having a predetermined interrelationship to produce sensor measurements;

calculating a reaction factor, a discharge factor, and an amplitude factor associated with the electrical output of the electrochemical sensor based on the sensor measurements at the three or more time intervals; and calculating the quantity of the electrochemically convertible substance in the gas sample using an arithmetic equation based on the reaction factor, the discharge factor and the amplitude factor.

2. The method of claim 1 wherein operation of calculating the quantity of the electrochemically convertible substance comprises:

calculating the arithmetic equation of a form $$quantity = k \cdot \left(\frac{1}{a} - \frac{1}{b}\right),$$

wherein quantity represents the quantity of the electrochemically convertible substance in the gas sample, k represents the amplitude factor, a represents the discharge factor, and b represents the reaction factor.

3. The method of claim 1 wherein the operation of calculating a reaction factor, a discharge factor, and an amplitude factor comprises:

calculating the discharge factor from an equation of a form $$a = -\frac{\ln\left[\left(\frac{y_{2t}}{y_t} + \sqrt{\left|2 \cdot \frac{y_{4t}}{y_{2t}} - \left(\frac{y_{2t}}{y_t}\right)^2\right|}\right)/2\right]}{t},$$

wherein $y_t$ is a sensor measurement at time t, $y_{2t}$ is a sensor measurement at time 2t, and $y_{4t}$ is a sensor measurement at time 4t.

4. The method of claim 1 wherein the operation of calculating a reaction factor, a discharge factor, and an amplitude factor comprises:

calculating the reaction factor from an equation of a form $$b = -\frac{\ln\left[\left(\frac{y_{2t}}{y_t} - \sqrt{\left|2 \cdot \frac{y_{4t}}{y_{2t}} - \left(\frac{y_{2t}}{y_t}\right)^2\right|}\right)/2\right]}{t},$$

wherein $y_t$ is a sensor measurement at time t, $y_{2t}$ is a sensor measurement at time 2t, and $y_{4t}$ is a sensor measurement at time 4t.

5. The method of claim 1 wherein the operation of calculating a reaction factor, a discharge factor, and an amplitude factor comprises:

calculating the amplitude factor from an equation of a form $$k = \frac{y_t}{\sqrt{\left|2 \cdot \frac{y_{4t}}{y_{2t}} - \left(\frac{y_{2t}}{y_t}\right)^2\right|}},$$

wherein $y_t$ is a sensor measurement at time t, $y_{2t}$ is a sensor measurement at time 2t, and $y_{4t}$ is a sensor measurement at time 4t.

6. The method of claim 1 wherein the electrochemically convertible substance is ethanol.

7. The method of claim 1 wherein the operation of calculating a reaction factor, a discharge factor, and an amplitude factor is performed using measurements of the electrical output of the electrochemical sensor at time t, time 2t, and time 4t.

8. A method of identifying an electrochemically convertible substance existing in a gas sample, the method comprising:

introducing the gas sample into an electrochemical sensor wherein at least a portion of the gas sample is electrochemically converted to produce an electrical output;

measuring the electrical output of the electrochemical sensor at three or more time intervals having a predetermined interrelationship to produce sensor measurements;

calculating a reaction factor and a discharge factor associated with the electrical output of the electrochemical sensor based on the sensor measurements at the three or more time intervals;

comparing a combination of the reaction and discharge factors to a combination of predetermined reaction and discharge factors associated with one or more predetermined reactants; and identifying the electrochemically convertible substance as one of the one or more predetermined reactants existing in the gas sample, if the combination of the reaction and discharge factors matches the combination of predetermined reaction and discharge factors associated with the one predetermined reactant relative to a predetermined deviation.

9. The method of claim 8 wherein the operation of calculating a reaction factor and a discharge factor comprises:

calculating the discharge factor from an equation of a form $$a = -\frac{\ln\left[\left(\frac{y_{2t}}{y_t} + \sqrt{\left|2 \cdot \frac{y_{4t}}{y_{2t}} - \left(\frac{y_{2t}}{y_t}\right)^2\right|}\right)/2\right]}{t},$$

wherein $y_t$ is a sensor measurement at time t, $y_{2t}$ is a sensor measurement at time 2t, and $y_{4t}$ is a sensor measurement at time 4t.

10. The method of claim 8 wherein the operation of calculating a reaction factor and a discharge factor comprises:

calculating the reaction factor from an equation of a form $$b = -\frac{\ln\left[\left(\frac{y_{2t}}{y_t} - \sqrt{\left|2 \cdot \frac{y_{4t}}{y_{2t}} - \left(\frac{y_{2t}}{y_t}\right)^2\right|}\right)/2\right]}{t},$$

wherein $y_t$ is a sensor measurement at time t, $y_{2t}$ is a sensor measurement at time 2t, and $y_{4t}$ is a sensor measurement at time 4t.

11. The method of claim 8 wherein the electrochemically convertible substance is an alcohol.

12. The method of claim 8 wherein the operation of calculating a reaction factor and a discharge factor is performed using measurements of the electrical output of the electrochemical sensor at time t, time 2t, and time 4t.

13. The method of claim 8 wherein the comparing operation comprises:

comparing the reaction factor to the predetermined reaction factor associated with a predetermined reactant; and comparing the discharge factor to the predetermined discharge factor associated with a predetermined reactant.

14. The method of claim 8 wherein the identifying operation comprises:

identifying the electrochemically convertible substance as one of the one or more predetermined reactants existing in the gas sample, if the reaction factor matches the predetermined reaction factor associated with the one predetermined reactant relative to a predetermined reaction factor deviation and the discharge factor matches the predetermined discharge factor associated with the one predetermined reactant relative to a predetermined discharge factor deviation.

* * * * *